(12) United States Patent
Neilson et al.

(10) Patent No.: US 11,035,754 B2
(45) Date of Patent: Jun. 15, 2021

(54) SINGLE-ENDED PROBING THROUGH A MULTIMODE FIBER HAVING DISTRIBUTED REFLECTORS

(71) Applicant: Nokia Technologies Oy, Espoo (FI)

(72) Inventors: David Neilson, Old Bridge, NJ (US);
Peter Winzer, Aberdeen, NJ (US);
Nicolas Fontaine, Keyport, NJ (US);
Haoshuo Chen, Aberdeen, NJ (US);
Roland Ryf, Aberdeen, NJ (US)

(73) Assignee: NOKIA TECHNOLOGIES OY, Espoo (FI)

( * ) Notice: Subject to any disclaimer, the term of this patent is extended or adjusted under 35 U.S.C. 154(b) by 116 days.

(21) Appl. No.: 16/230,115

(22) Filed: Dec. 21, 2018

(65) Prior Publication Data
US 2020/0200646 A1 Jun. 25, 2020

(51) Int. Cl.
*G01M 11/00* (2006.01)
*A61B 5/00* (2006.01)
*G01B 9/02* (2006.01)

(52) U.S. Cl.
CPC ....... *G01M 11/3172* (2013.01); *A61B 5/0066* (2013.01); *G01B 9/02023* (2013.01); *G01B 9/02091* (2013.01)

(58) Field of Classification Search
CPC .......... G01M 11/3172; G01M 11/3181; A61B 5/0066; G01D 5/35316; G01D 5/35306; G01B 9/02023; G01B 9/02091
See application file for complete search history.

(56) References Cited

U.S. PATENT DOCUMENTS

| 7,174,067 B2 | 2/2007 | Murshid et al. |
| 7,639,909 B2 | 12/2009 | Murshid et al. |
| 8,310,769 B2 | 11/2012 | Mizusawa |
| (Continued) | | |

FOREIGN PATENT DOCUMENTS

| WO | WO2018064397 A1 | 4/2018 |
| WO | WO2018125633 A1 | 7/2018 |

OTHER PUBLICATIONS

Extended European Search Report for corresponding European application No. 19217317.7; dated May 4, 2020 (8 pages).
(Continued)

*Primary Examiner* — Hwa Andrew Lee
(74) *Attorney, Agent, or Firm* — Mendelsohn Dunleavy, P.C.; Yuri Gruzdkov

(57) ABSTRACT

An optical frequency-domain reflectometer (OFDR) capable of estimating the transfer matrix of a multimode optical fiber using mode-selective measurements performed from a single end of the fiber. In an example embodiment, the multimode optical fiber includes distributed reflectors designed to generate relatively strong light reflections along the length of the fiber at a desired spatial resolution. The embodiments may employ a signal-processing algorithm to estimate the fiber's transfer matrix by estimating segment transfer matrices corresponding to the fiber segments located between different ones of the distributed reflectors. Different embodiments of the disclosed OFDR can beneficially be adapted for use in different applications, such as fiber-optic component and module characterization, distributed optical sensing, biomedical imaging, OCT, etc.

13 Claims, 4 Drawing Sheets

(56) References Cited

U.S. PATENT DOCUMENTS

| | | | |
|---|---|---|---|
| 8,320,769 | B2 | 11/2012 | Essiambre et al. |
| 8,355,638 | B2 | 1/2013 | Essiambre et al. |
| 8,705,913 | B2 | 4/2014 | Winzer et al. |
| 9,680,599 | B2 | 6/2017 | Kakande |
| 10,345,192 | B2 * | 7/2019 | Chen .............. H04J 14/04 |
| 10,401,883 | B2 * | 9/2019 | Swanson ............. G01J 3/4406 |
| 2006/0013523 | A1 | 1/2006 | Childlers et al. |
| 2013/0315532 | A1 | 11/2013 | Xie et al. |
| 2015/0124266 | A1 | 5/2015 | Davis et al. |
| 2015/0309249 | A1 | 10/2015 | Murshid et al. |
| 2016/0233959 | A1 | 8/2016 | Murshid et al. |
| 2016/0242653 | A1 | 8/2016 | Rourke et al. |
| 2018/0078317 | A1 | 3/2018 | Mariampillai et al. |
| 2018/0188019 | A1 | 7/2018 | Eggleston |
| 2018/0284304 | A1 | 10/2018 | Barfoot et al. |

OTHER PUBLICATIONS

Carpenter, Joel, et al. "First demonstration of principal modes in a multimode fibre." 2014 The European Conference on Optical Communication (ECOC). IEEE, 2014: 3 pages.

"1310/CWDM MUX/DEMUX Plug-in Module," Specifications, 2015; as retrieved from https://www.finisar.com/sites/default/files/downloads/1310_cwdm_mux_demux_plug-in_module_product_specification_rev_e.pdf; 2 pages.

"40 Channels C21-C60 Dual Fiber DWDM Mux Demux + Monitor Port," 1U Rack Mount, LC/UPC Datasheet, FS.Com Data Center & Cloud Computing Infrastruture Solutions; 2018.

"MX: Modal Mux/Demux Datasheet," 2015, as retrieved from http://kylia.com/kylia/wp-content/u.ploads/2015/02/datasheet-MX-v2.0.pdf, pp. 1-5.

"Fiber Space (De)Multiplexer based on Photonic Lantern," Phoenix Photonics, 2014, Technical Brief #8, as retrieved from http://www.phoenixphotonics.com/website/technology/documents/PhotonicLantern0414_v1.pdf. pp. 1-6.

"Proteus-S," CAILabs, 2017, General Specifications; 1 pages.

"Proteus-C," CAILabs, 2015, Datasheet; 2 pages.

Carpenter, J., et al. "Characterization of multimode fiber by selective mode excitation." Journal of lightwave technology 30.10 (2012): 1386-1392.

Mahanta, D.K. "Design of Uniform Fiber Bragg grating using Transfer matrix method." Int J Comput Eng Res 3 (2013): 8-13.

Soller, Brian J., et al. "High resolution optical frequency domain reflectometry for characterization of components and assemblies." Optics Express 13.2 (2005): 666-674.

Ryf, R., et al. "Low-loss mode coupler for mode-multiplexed transmission in few-mode fiber." OFC/NFOEC. IEEE, 2012; 3 pages.

Velázquez-Benítez, A. M., et al. "Scaling the fabrication of higher order photonic lanterns using microstructured preforms." European Conference on Optical Communication (ECOC). IEEE, 2015, 3 pages.

"Course Wavelength Division Multiplexer/Demultiplexer (CWDM) Module," WaveReady, DataSheet, 2015, as retrieved from: www.lumentum.com, pp. 1-4.

Melati, D., et al. "Reconfigurable photonic integrated mode (de) multiplexer for SDM fiber transmission." Optics express 24.12 (2016): 12625-12634.

\* cited by examiner

400

SINGLE-ENDED PROBING THROUGH A MULTIMODE FIBER HAVING DISTRIBUTED REFLECTORS

BACKGROUND

Field

Various example embodiments relate to fiber optics and, more specifically but not exclusively, to optical imaging and sensing using multimode fibers.

Description of the Related Art

This section introduces aspects that may help facilitate a better understanding of the disclosure. Accordingly, the statements of this section are to be read in this light and are not to be understood as admissions about what is in the prior art or what is not in the prior art.

Technologies for imaging interiors of structures, e.g., in vivo imaging of interiors of animals, are useful for monitoring health and for making medical diagnoses. One class of such imaging technologies is optical coherence tomography (OCT). OCT produces images based on reflective or refractive index variations in a region of the animal or structure being imaged. Some forms of OCT involve the use of multimode fibers.

SUMMARY OF SOME SPECIFIC EMBODIMENTS

Disclosed herein are various embodiments of an optical frequency-domain reflectometer (OFDR) capable of estimating the transfer matrix of a multimode optical fiber using mode-selective measurements performed from a single end of the multimode optical fiber. In an example embodiment, the multimode optical fiber includes distributed reflectors designed to generate relatively strong light reflections along the length of the fiber at a desired spatial resolution. For example, the reflectors may be regularly or even continuously distributed along part or all of said multimode optical fiber. The embodiments may employ a signal-processing algorithm to estimate the fiber's transfer matrix by estimating segment transfer matrices corresponding to the fiber segments located between different ones of the distributed reflectors. For example, such estimates of segment transfer matrices may be performed in an iterative manner, each iteration involving a next segment located sequentially farther from the probed end of the multimode optical fiber.

Different embodiments of the disclosed OFDR can beneficially be adapted for use in different applications, such as fiber-optic component and module characterization, distributed optical sensing, biomedical imaging, OCT, etc.

According to an example embodiment, provided is an apparatus comprising: a tunable laser configured to generate probe light and controllable to sweep a wavelength of said probe light; a first configurable optical filter to transmit a received part of said probe light primarily to a selectable spatial propagation mode of the multimode optical fiber at a first end thereof; a second configurable optical filter to receive light from the first end of the multimode optical fiber in response to reflection therein and to transmit a portion of said received light, said portion being primarily received from a chosen spatial propagation mode of said multimode optical fiber at the first end; an optical interferometer connected to mix other part of the probe light with the light transmitted by the second configurable optical filter to generate an optical interference signal; and a digital signal processor configured to determine a single-direction transfer matrix of said multimode optical fiber from measurements of said optical interference signal.

According to another example embodiment, provided is an apparatus comprising: an optical frequency-domain reflectometer having a tunable light source, an optical interferometer, and an optical receiver, the optical interferometer including a multimode optical fiber having reflectors distributed there along, the optical interferometer being configured to generate output light in response to receiving probe light from the tunable light source, the apparatus being able to selectively form the output light to primarily correspond to light transmitted to a selected spatial propagation mode at an end of the multimode optical fiber and light outputted at the end of the multimode optical fiber from a chosen spatial propagation mode of the multimode optical fiber; and a digital signal processor configured to estimate a single-direction fiber transfer matrix in response to measurements of the output light performed by the optical receiver.

BRIEF DESCRIPTION OF THE DRAWINGS

Other aspects, features, and benefits of various disclosed embodiments will become more fully apparent, by way of example, from the following detailed description and the accompanying drawings, in which.

DETAILED DESCRIPTION

At least some embodiments disclosed herein may benefit from the use of at least some features disclosed in U.S. Patent Application Publication No. 2018/0188019, which is incorporated herein by reference in its entirety.

When an object is imaged through a multimode fiber, light from the object being imaged typically propagates through the fiber on different modes thereof. Due to modal dispersion and mode mixing, such a multimode optical fiber may cause the image produced by the light received from the end of the fiber to appear blurred.

Mode mixing in a multimode fiber can mathematically be represented by a transfer matrix H that describes the amplitude and phase relationship between the light input to various modes of the multimode fiber and the light output from the various modes of the multimode fiber. More specifically, each matrix element $H_{ij}$ of the transfer matrix H describes the amplitude and phase relationship between the j-th spatial mode at the first (e.g., proximal) end of the fiber and the light received from the i-th spatial mode at the second (e.g., distal) end of the fiber. The transposed transfer matrix, i.e., $H^T$, similarly describes the amplitude and phase relationship between the light applied to the various spatial modes at the second end of the fiber and the light received from the various spatial modes at the first end of the fiber. The transfer matrix H is an N×N matrix, where N is the number of guided modes in the fiber.

Some image-processing techniques, known to those skilled in the pertinent art, are capable of significantly improving the quality of (e.g., removing the blur from) images obtained by light transmitted through a multimode optical fiber. However, such image-processing techniques typically require the knowledge of the transfer matrix H of the fiber through which the image is acquired.

Conventional methods for measuring the transfer matrix H typically require relatively unencumbered access to both ends of the fiber, e.g., to excite various modes at one end and to detect light received in various modes at the other end. However, in many imaging (e.g., OCT) applications, the distal end of the fiber is not directly accessible, e.g., because it is inserted deep into a bodily cavity. The insertion also typically causes the fiber to be bent into a shape that is not readily controllable. When the fiber is bent, stressed, or otherwise perturbed, the transfer matrix H typically changes, thereby rendering prior (e.g., before the insertion) measurements of the transfer matrix H substantially unusable.

Various embodiments disclosed herein address this and some other related problems in the state of the art by providing methods and apparatus for measuring the transfer matrix H from the single accessible (e.g., proximal) end of the fiber, without requiring separate access to the other (e.g., distal) end of the fiber.

Figure 1:
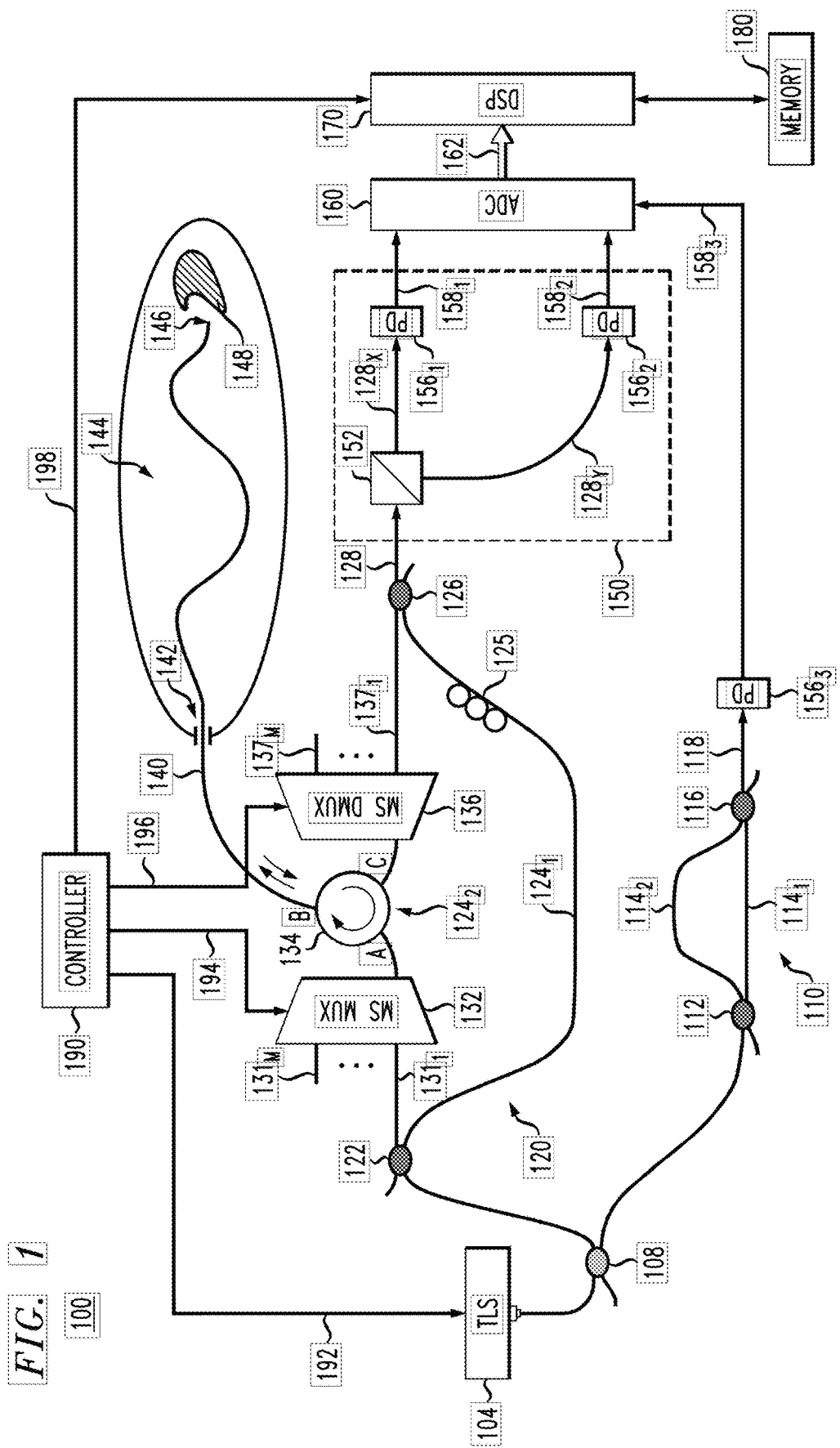
FIG. 1 shows a block diagram of an optical system according to an embodiment.

FIG. 1 shows a block diagram of an optical system 100 according to an embodiment. Various embodiments of system 100 may be adapted for remote optical characterization or remote optical communication applications, e.g., for fiber-optic component and module characterization, distributed optical sensing, biomedical imaging, OCT, or other applications. In the corresponding embodiments, system 100 may be a subsystem of the larger system designed for one of these specific applications.

System 100 comprises a tunable light source (TLS) 104, interferometers 110 and 120, and an optical receiver 150. Electrical output signals $158_1$ and $158_2$ generated by receiver 150 are converted into a digital form using an analog-to-digital converter (ADC) 160, and the resulting digital samples 162 are processed by a digital signal processor (DSP) 170. A memory 180 operatively coupled to DSP 170 is configured to store the data representing the various digital signals received and/or generated by DSP 170, e.g., the sequentially temporally received signal samples. An electronic controller 190 can be used to control and/or communicate with the various components of system 100, e.g., as further described below.

System 100 further comprises a multimode optical fiber 140 connected to interferometer 120 as indicated in FIG. 1. Fiber 140 includes optical reflectors distributed in a suitable manner along the length of the fiber, e.g., along part or all of the length. In different embodiments, the length of fiber 140 may range from 10 cm to 100 m, or even longer for short reach optical communication applications. Example embodiments of fiber 140 are described in more detail below in reference to FIGS. 2 and 3.

For illustration purposes, fiber 140 is shown in FIG. 1 as being inserted through an opening 142 into a cavity 144. A distal end 146 of fiber 140 is placed in proximity to an object 148 located inside cavity 144 such that at least some parts of said object can be optically probed (e.g., illuminated and reflectively imaged to form 2-dimensional or 3-dimensional pixelated images of said parts) through the fiber. Inside cavity 144, fiber 140 may be bent into a substantially arbitrary shape, e.g., as indicated in FIG. 1. The delimiters (e.g., walls) of cavity 144 and the relatively small size of opening 142 encumber access to distal end 146 in a manner that does not allow the light emitted out from the distal end to be directly detected thereat.

In an example embodiment, TLS 104 may be a pulsed or continuous-wave light source and may be an about continuously wavelength-tunable, external-cavity laser diode operating in the C and/or L communication bands. An example tuning range may be, e.g., from about 2 nm to about 40 nm and be spectrally located near 1550 nm. The tuning rate may be, e.g., between 20 and 80 nm/s. The wavelength (frequency) sweep of TLS 104 can be controlled, e.g., by way of a control signal 192 applied to the TLS by controller 190.

An asymmetric optical coupler 108 may be coupled to the output of TLS 104 and may be operated to split the light beam generated by the TLS into two portions. The first portion is applied to interferometer 110. The second portion is applied to interferometer 120. The intensity ratio between the first and second portions can be, e.g., 10:90 or 5:95.

Interferometer 110 comprises interferometer arms $114_1$ and $114_2$ connected between optical couplers 112 and 116. In an example embodiment, optical couplers 112 and 116 can be 3-dB couplers. The non-zero differential delay of interferometer arms $114_1$ and $114_2$ is selected such that an optical interference signal 118 generated at the output of optical coupler 116 has a desired (e.g., radio) beat frequency as the wavelength of TLS 104 is temporally swept. A photodetector (e.g., a photodiode) $156_3$ operates to convert optical interference signal 118 into a corresponding electrical signal $158_3$ having the beat frequency. Signal $158_3$ is then used, as known in the pertinent art, to trigger data acquisition at the outputs of receiver 150.

Interferometer 120 comprises interferometer arms $124_1$ and $124_2$ connected between optical couplers 122 and 126. In an example embodiment, optical couplers 122 and 126 can be 3-dB couplers. An optical interference signal 128 generated at the output of optical coupler 126 is applied to receiver 150.

In some embodiments, interferometer arm $124_1$ may include an optional polarization controller 125. Polarization controller 125 can be used, e.g., to monitor changes in the state of polarization in interferometer arm $124_2$ and/or measure the transfer matrix H in a polarization-resolved manner.

In an example embodiment, interferometer arm $124_2$ comprises a mode-selective multiplexer (MS MUX) 132, a circulator 134, and a mode-selective demultiplexer (MS DMUX) 136. The output of MS MUX 132 is connected to port A of circulator 134. The input of MS DMUX 136 is connected to port C of circulator 134. The proximal end of fiber 140 is connected to port B of circulator 134. In operation, circulator 134 couples light received at port A into port B, and couples light received at port B into port C. The light coupling between the ports of circulator 134 is performed in a mode-preserving manner. In other embodiments, the circulator 134 may be replaced by another optical device enabling the transmission of light from MS MUX 132 to the proximal end of optical fiber 140 and enabling reception of light received from the proximal end of the optical fiber by MS DMUX 136.

In operation, probe light is directed from TLS 104, through MS MUX 132 and circulator 134, then through the proximal end of fiber 140, and into the fiber. Light reflected back by the optical reflectors of fiber 140 or by reflection near the distal end thereof is then directed from the proximal end of the fiber, through circulator 134 and through MS DMUX 136, to optical coupler 126.

In an example embodiment, MS MUX 132 operates to spatially shape (e.g., phase and/or intensity filter), and e.g., to optionally polarization shape, the optical signals applied to the M input ports $131_1$-$131_M$ thereof to cause each of the resulting spatially shaped signals to have, e.g., a transverse electric-field distribution that will substantially match the electric-field distribution of the corresponding guided (e.g., LP) mode when received at the proximate end-face of fiber 140. MS MUX 132 then combines the spatially shaped signals and applies the resulting combined optical signal to port A of circulator 134. In different embodiments, the number M can be a different respective positive integer, e.g., 1, 2, 3, and so on.

MS MUX 132 can be (re)configured in response to a control signal 194 generated by controller 190, e.g., to select different respective modes for the different input ports $131_m$. The selected mode can be changed for each port, if appropriate or necessary for the intended function or mode-selective operation of system 100, e.g., transverse-spatial-mode selective light-excitation of the multimode optical fiber 140 by the TLS 104 and optionally polarization propagation-mode selective light-excitation of the multimode optical fiber 140.

In the shown embodiment, only one input port, i.e., input port $131_1$, of MS MUX 132 is connected to receive light from TLS 104. Thus, in this embodiment, MS MUX 132 operates as a transverse spatial mode-selective filter that can be configured and reconfigured to selectively excite one transverse-spatial propagation mode of the multimode optical fiber 140 at a time. However, in an alternative embodiment, two or more input ports $131_m$ of MS MUX 132 may be connected to receive light from TLS 104, e.g., as described in more detail below. MS MUX 132 may also optionally be (re)configured as a polarization mode filter, e.g., to enable, respectively, the excitation of selected polarizations of transverse-spatial propagation modes of the multimode optical fiber 140.

MS DMUX 136 operates to: (i) split into M portions the optical signal received from port C of circulator 134 and (ii) spatially shape (e.g., phase and/or intensity filter and optionally polarization filter) each of the M portions to extract therefrom the light received via corresponding one(s) of the M selected transverse-spatial propagation modes of optical fiber 140. The resulting M optical signals are then directed to output ports $137_1$-$137_M$, respectively, of MS DMUX 136.

MS DMUX 136 can be (re)configured in response to a control signal 196 generated by controller 190, e.g., to select output light from different respective ones of the transverse spatial propagation modes of the multimode optical fiber 140 to the different output ports 131. The selected mode(s) can be changed for each port, if appropriate or necessary for the intended function or mode of operation of system 100.

In the shown embodiment, only one output port, i.e., output port $137_1$, of MS DMUX 136 is connected to receiver 150. Thus, in this embodiment, MS DMUX 136 operates as a mode-selective filter that selects, e.g., light from one transverse-spatial propagation mode of the multimode optical fiber 140 at a time and may optionally select based on polarization of said mode. However, in alternative embodiments, two or more output ports $137_m$ of MS DMUX 133 may be connected to multiple respective instances (e.g., nominal copies, not explicitly shown in FIG. 1) of receiver 150, e.g., as described in more detail below and/or as would be understood by the person of ordinary skill in the pertinent art based on the present disclosure.

In some embodiments, MS MUX 132 and MS DMUX 136 can be implemented using two respective instances (e.g., nominal copies) of the same physical device connected to transmit light signals in opposite directions, i.e., by inverting optical inputs with optical outputs.

Example optical circuits and devices that can be used to implement MS MUX 132 and MS DMUX 136 are disclosed, e.g., U.S. Pat. Nos. 8,355,638, 8,320,769, 7,174,067, and 7,639,909, and U.S. Patent Application Publication Nos. 2016/0233959 and 2015/0309249, all of which are incorporated herein by reference in their entirety. Some embodiments of MS MUX 132 and/or MS DMUX 136 can benefit from the use of optical circuits and devices disclosed in: (i) Daniele Melati, Andrea Alippi, and Andrea Melloni, "Reconfigurable Photonic Integrated Mode (De)Multiplexer for SDM Fiber Transmission," Optics Express, 2016, v. 24, pp. 12625-12634; and (ii) Joel Carpenter and Timothy D. Wilkinson, "Characterization of Multimode Fiber by Selective Mode Excitation," JOURNAL OF LIGHTWAVE TECHNOLOGY, vol. 30, No. 10, pp. 1386-1392, both of which are also incorporated herein by reference in their entirety.

In some embodiments, MS MUX 132 and MS DMUX 136 can be implemented using at least some mode-selective devices that are commercially available, e.g., from CAILabs, Phoenix Photonics, and/or Kylia, as evidenced by the corresponding product-specification sheets, which are also incorporated herein by reference in their entirety.

In the illustrated example embodiment, receiver 150 is a polarization-sensitive receiver that comprises a polarization beam splitter 152 and photodetectors (PDs) $156_1$ and $156_2$. PBS 152 operates to split optical signal 128 into two orthogonal polarization components, which are labeled in FIG. 1 using the reference labels $128_X$ and $128_Y$, respectively, e.g., to split the optical signal based on either orthogonal linear or orthogonal circular polarizations. Photodetectors $156_1$ and $156_2$ then operate to convert optical signals $128_X$ and $128_Y$ into the corresponding electrical signals, which are labeled in FIG. 1 using the reference labels $158_1$ and $158_2$, respectively. ADC 160 digitizes electrical signals $158_1$ and $158_2$, when triggered by signal $158_3$, to generate digital samples 162 for further processing in DSP 170. A control signal 198 supplied by controller 190 enables DSP 170 to sort and/or annotate different sets of digital samples 162 to specify the respective pertinent configuration parameters corresponding to each set. For example, such pertinent configuration parameters may include annotations of corresponding excitation and reception transverse-spatial propagation modes for the light to and from the multimode optical fiber 140 with or without designation(s) of polarization modes.

An example operating method that can be used to operate system 100 is described below in reference to FIG. 4.

An example signal-processing method that can be used to process digital samples 162 in DSP 170 is described below in reference to FIG. 5.

In the above-mentioned alternative embodiment, more than one (e.g., all M) input ports $131_m$ can be connected to receive probe light from TLS 104. The corresponding modification may include: (i) replacing optical coupler 122 by a 1×M optical coupler, e.g. either an optical power splitter or an optical wavelength demultiplexer (DEMUX); and (ii) connecting the M outputs of that optical coupler to input ports $131_1$-$131_M$, respectively. For example, modification with the optical DEMUX may send a different respective wavelength to each input port $131_1$-$131_M$. Further modifications may include: (i) inserting an additional 1×M optical coupler, e.g., an optical power splitter or an optical wavelength demultiplexer, into interferometer arm $124_1$; (ii)

adding (M−1) sets of optical couplers 126 and receivers 150 such that each of output ports $137_1$-$137_M$ can have a respective circuit analogous to that shown in FIG. 1 coupled thereto; and (iii) connecting the added receivers to DSP 170, e.g., using one or more additional ADCs. For example, this second modification with the optical DEMUX may cause each output port $137_1$-$137_M$ to output light of a different wavelength.

A person of ordinary skill in the art will understand that said alternative embodiment enables multiple combinations of input/output modes of fiber 140 to be probed per wavelength sweep of TLS 104, e.g., based on the simultaneous use of different probe wavelengths and the modifications introducing optical DEMUXes as already described. For comparison, the embodiment shown in FIG. 1 can be used to probe a single combination of (input mode/output mode) of fiber 140 per wavelength sweep of TLS 104, e.g., as described in reference to FIG. 4.

Figure 2:
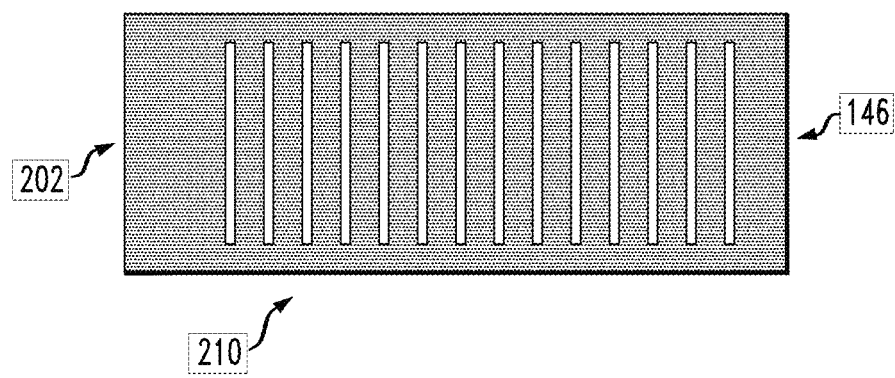
FIG. 2 shows a schematic view of a multimode fiber that can be used in the optical system of FIG. 1 according to an embodiment.

FIG. 2 shows a schematic view of fiber 140 according to an embodiment. In this embodiment, fiber 140 has a continuous distributed Bragg reflector (DBR) 210 along the fiber length. A first (proximal) end 202 of this fiber 140 is configured to be connected to port B of circulator 134, e.g., using a suitable adapter or connector (not explicitly shown in FIG. 2). As already indicated above, distal end 146 of fiber 140 is suitable for insertion into cavity 144 (also see FIG. 1).

The transmission/reflection characteristics of DBR 210 can be selected such that: (i) a first relatively large portion of the input light applied to end 202 can reach end 146; and (ii) a second relatively large portion of the input light applied to end 202 is reflected by DBR 210 and returned back to end 202. For example, the first portion can be such as to enable imaging of object 148 through fiber 140. The second portion can be such as to enable measurements of the transfer matrix H, e.g., as described further below. In some such multimode optical fibers 140, the second relatively large portion may be, e.g., small enough so that multiple reflections of the same light along the length of the multimode optical fiber 140 can be substantially neglected when determining a particular element of the optical transfer or channel matrix of the multimode optical fiber 140 from measurement(s) of light reflected therein.

Figure 3:
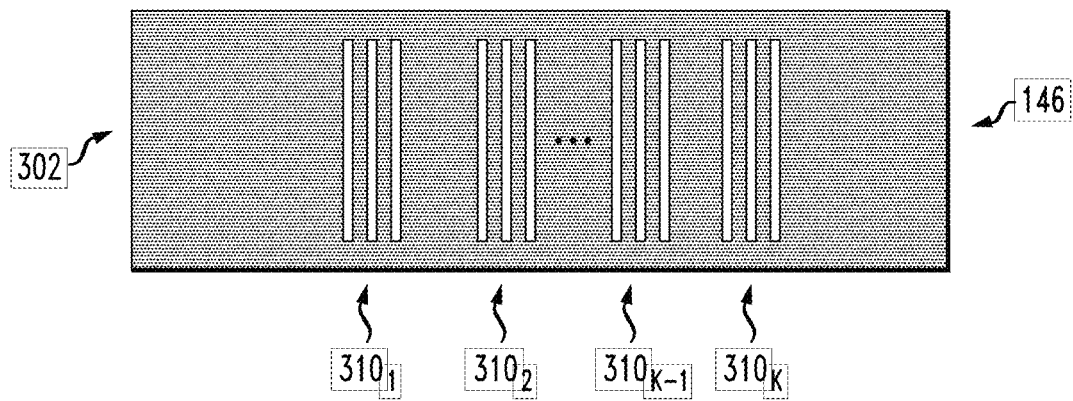
FIG. 3 shows a schematic view of a multimode fiber that can be used in the optical system of FIG. 1 according to an alternative embodiment.

FIG. 3 shows a schematic view of fiber 140 according to an alternative embodiment. In this embodiment, fiber 140 has a plurality of distinct DBRs $310_1$-$310_K$ along the fiber length. In an example embodiment, the distance between adjacent DBRs 310 can be several millimeters. A first (proximal) end 302 of this fiber 140 is connectable to port B of circulator 134. As already indicated above, distal end 146 of fiber 140 can be inserted into cavity 144. In some such multimode optical fibers 140, the plurality of DBRs $310_1$-$310_K$ may have a small enough combined reflectivity, e.g., such that reflection of the same light by multiple DBRs $310_1$-$310_K$ can be substantially neglected when determining the optical transfer or channel matrix for a short segment of the fiber 140 from measurement(s) of reflected light.

The transmission/reflection characteristics of DBRs $310_1$-$310_K$ can be selected such that: (i) a first relatively large portion of the input light applied to end 302 can reach end 146; and (ii) a second relatively large portion of the input light applied to end 302 is reflected by DBRs $310_1$-$310_K$ and returned back to end 302. In some embodiments, different DBRs $310_k$ may be nominally identical. In some other embodiments, different DBRs $310_k$ may differ from each other in one or more characteristics, such as reflectivity, spatial period, and/or separation from the adjacent DBRs $310_{k-1}$ and $310_{k+1}$.

Figure 4:
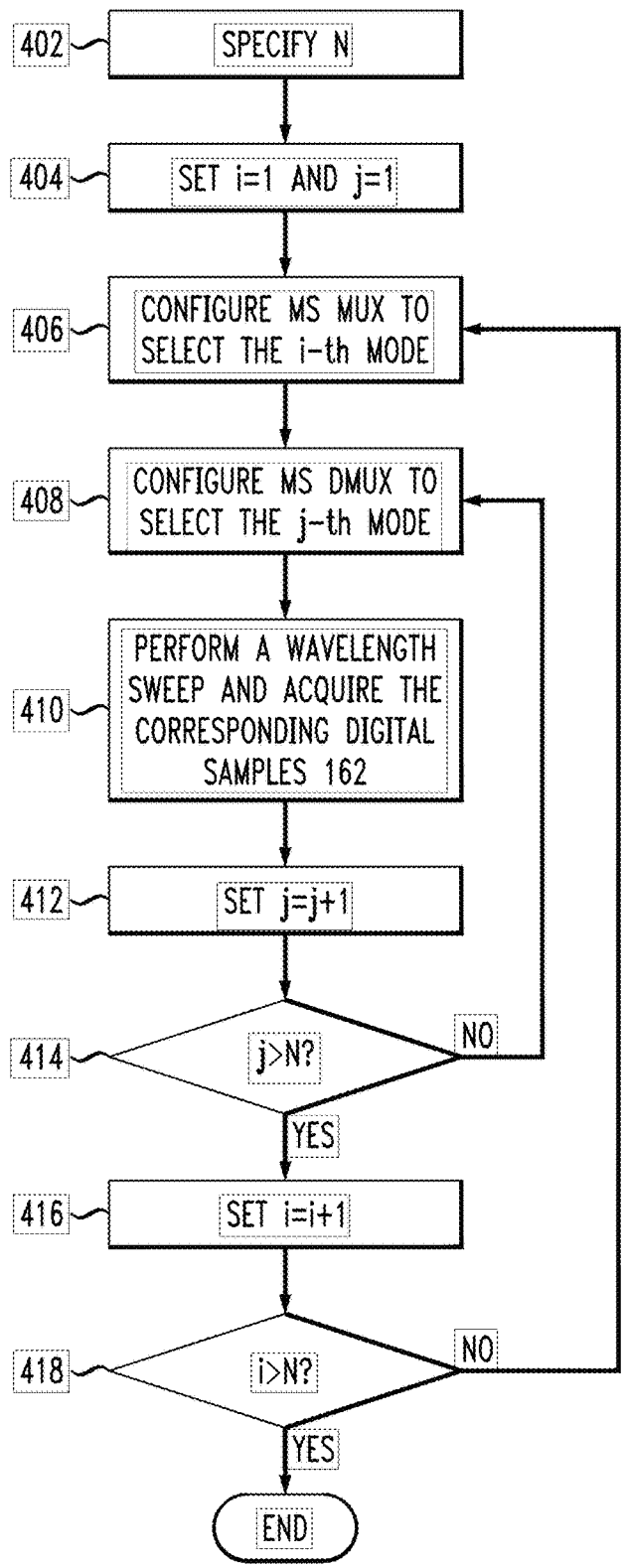
FIG. 4 shows a flowchart of a data-acquisition method that can be used to operate the optical system of FIG. 1 according to an embodiment.

FIG. 4 shows a flowchart of a data-acquisition method 400 that can be used to operate system 100 according to an embodiment. Method 400 is described in continuing reference to FIG. 1.

Method 400 begins at step 402, in which the number N corresponding to the currently connected fiber 140 is specified to controller 190, where N is the number of transverse-spatial and/or polarization propagation modes supported by the fiber. A person of ordinary skill in the art will understand that the number N depends on certain characteristics of the fiber in question and the operating wavelength λ.

For example, for a given wavelength λ, an optical fiber can typically support multiple guided transverse-spatial propagation modes if the normalized frequency parameter V (also referred to as the V number) is greater than about 2.405. Eq. (1) gives the expression for V:

$$V = \frac{2\pi a}{\lambda} NA \tag{1}$$

where a is the fiber-core radius, and NA is the numerical aperture. For a step-index fiber, the numerical aperture is given by Eq. (2):

$$NA = \sqrt{n_1^2 - n_2^2} \tag{2}$$

where $n_1$ is the refractive index of the fiber core, and $n_2$ is the refractive index of the fiber cladding.

The guided modes of the fiber can generally be classified as (i) transverse electric (TE) modes, for which the axial component of the electric field is zero; (ii) transverse magnetic (TM) modes, for which the axial component of the magnetic field is zero; and (iii) HE or EH modes, for which neither the axial component of the electric field nor the axial component of the magnetic field is zero. The designation of HE or EH depends on which of the electric (E) and magnetic (H) field components is dominant.

The refractive-index profiles of some commercially available step-index optical fibers have a relatively small (e.g., smaller than about 0.05) contrast Δ, which makes these fibers only weakly guiding. Eq. (3) gives the definition of Δ for a step-index fiber:

$$\Delta = \frac{n_1 - n_2}{n_1} \tag{3}$$

In the approximation of weak guidance for generally cylindrical fibers, the TE, TM, HE, and EH guided modes approximately become the modes that are conventionally referred to as the linearly polarized (LP) modes. Representative intensity and electric-field distributions of several low-order LP modes are graphically shown, e.g., in U.S. Pat. No. 8,705,913, which is incorporated herein by reference in its entirety.

Each transverse-spatial propagation mode can typically have two orthogonal polarization forms. Some transverse-spatial/polarization modes may be degenerate, e.g., in velocity and/or in angular momentum.

At step 404, the indices i and j are set to initial values, e.g., i=1 and j=1. The indexes i and j can be used to identify the corresponding set $S_{ij}$ of data acquired using the corresponding instance of step 410. For example, the respective row and column indices "i" and "j" of the element of the transfer matrix being measured.

At step 406, controller 190 generates control signal 194 to configure MS MUX 132 to selectively primarily or substantially only transmit light to the j-th propagation mode of fiber 140.

At step 408, controller 190 generates control signal 196 to configure MS DMUX 136 to selectively primarily or substantially only transmit light received from the i-th propagation mode of fiber 140.

At step 410, controller 190 generates control signal 192 to cause TLS 104 to perform a wavelength sweep. The resulting electrical signal $158_3$ triggers ADC 160 to digitize the corresponding electrical signals $158_1$ and $158_2$, thereby generating the corresponding (i, j)-th digital samples 162. In some embodiments, said digital samples 162 may need to be processed by DSP to derive therefrom the corresponding set $S_{ij}$. In an example embodiment, the set $S_{ij}$ represents a complex-valued time-dependent waveform $W_{ij}(t)$, with the different digital samples of the set $S_{ij}$ being the samples of the waveform $W_{ij}(t)$ corresponding to different respective times t. The set $S_{ij}$ is then saved in memory 180, e.g., for further processing using method 500 (see FIG. 5).

At step 412, the index j may be changed by one.

Step 414 serves to verify that the incremented value of the index j is still within the valid range, which is defined as $1 \leq j \leq N$. If the index j is within the valid range, then the processing of method 400 is directed back to step 408. Otherwise, the processing of method 400 is directed to step 416.

At step 416, the index i may be changed by one.

Step 418 serves to verify that the incremented value of the index i is still within the valid range, which is defined as $1 \leq i \leq N$. If the index i is within the valid range, then the processing of method 400 is directed back to step 406. Otherwise, the processing of method 400 is terminated.

Figure 5:
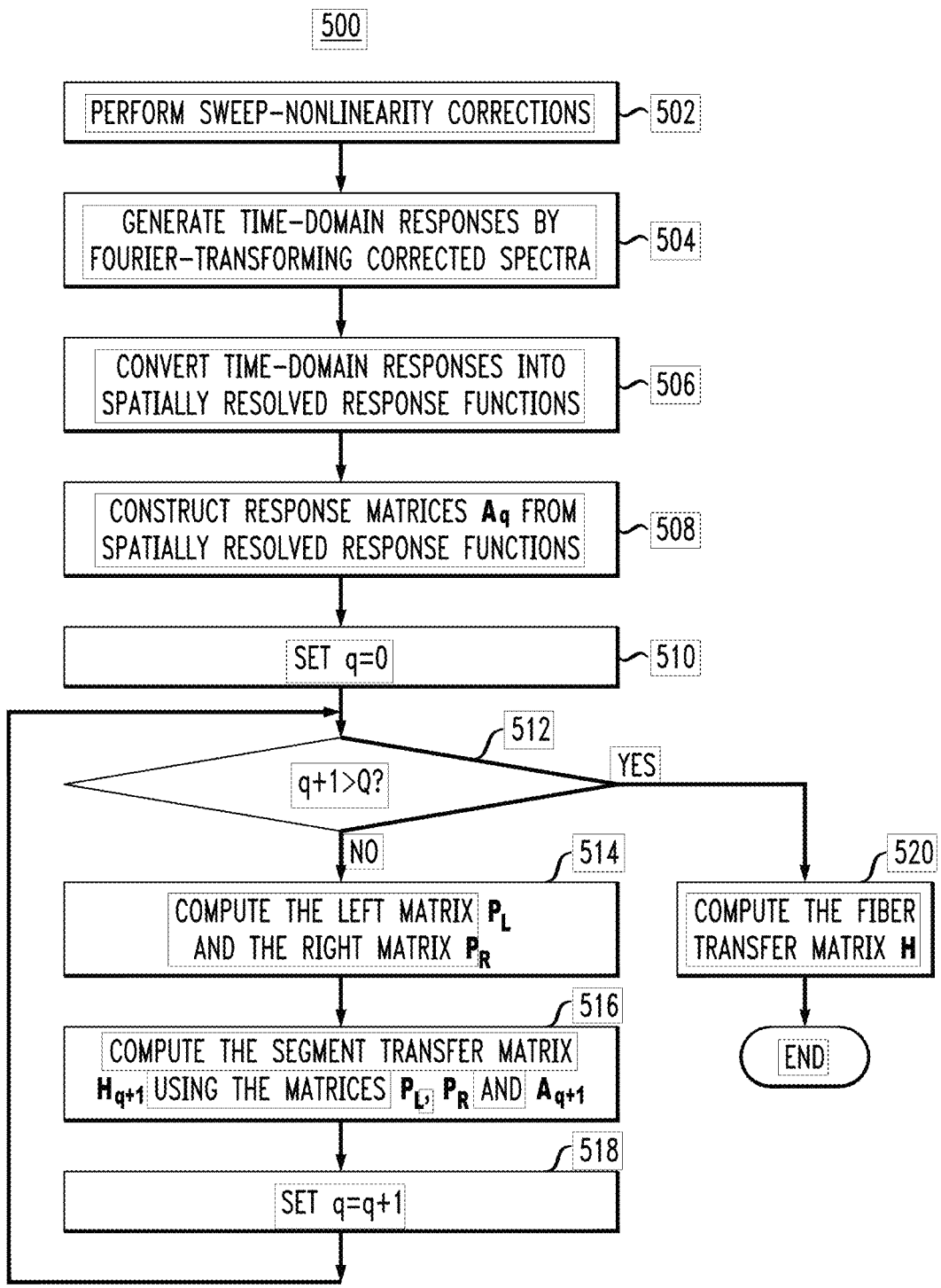
FIG. 5 shows a flowchart of a signal-processing method that can be used in the optical system of FIG. 1 according to an embodiment.

FIG. 5 shows a flowchart of a signal-processing method 500 that can be used in system 100 according to an embodiment. Method 500 uses the sets $S_{ij}$ (acquired using method 400) as inputs. Said sets $S_{ij}$ may be processed, e.g., as described below, to estimate the transfer matrix H of fiber 140.

At step 502 of method 500, the sets $S_{ij}$ may be, e.g., optionally processed to perform corrections that take into account possible deviations (if any) due to a linear wavelength sweep, i.e., of TLS 104, from a linear function expressed by Eq. (4):

$$\lambda(t) = \lambda_1 + (\lambda_2 - \lambda_1)\frac{t}{t_s} \qquad (4)$$

where $\lambda_1$ and $\lambda_2$ are the start and end wavelengths of the sweep, respectively; and $t_s$ is the duration of the wavelength sweep. The result of the processing performed at step 502 is the plurality of digital spectra $W'_{ij}(\lambda)$, for which time t and wavelength $\lambda(t)$ have a linear relationship in accordance with Eq. (4).

At step 504, each of digital spectra $W'_{ij}(\lambda)$ generated at step 502 is Fourier-transformed. Prior to the Fourier transform, the argument k may need to be converted into the beat frequency f. The result of the processing performed at step 504 is the plurality of digital time-domain responses $A_{ij}(\tau)$, where $\tau$ is the time of flight of the corresponding portion of the probe light through fiber 140.

At step 506, each of time-domain responses $A_{ij}(\tau)$ is converted into the corresponding response function $A_{ij}(x)$, where x is the distance from the proximal end (e.g., 202, FIG. 2, or 302, FIG. 3) along the span of fiber 140. This conversion can be performed, e.g., using the known linear relationship between the time of flight $\tau$ and the distance x. The processing performed at step 506 thereby generates $N^2$ response functions $A_{ij}(x)$. Each of the response functions $A_{ij}(x)$ is a discrete function in which the argument x, i.e., x is the reflection distance or location in the multimode optical fiber 140, can have one of the values $x_1 < x_2 < \ldots < x_Q$, where Q is the number of digital samples in the response function $A_{ij}(x)$.

At step 508, the response functions $A_{ij}(x)$ are used to generate response matrices $A_q$, where $q=1, 2, \ldots, Q$. The matrix elements of each response matrix $A_q$ are expressed by Eq. (5) as follows:

$$A_{ij}^{(q)} = A_{ij}(x_q) \qquad (5)$$

The response function $A_{ij}(x)$ is, e.g., the (i, j)-th element of a roundtrip transfer matrix that includes a back reflection in the multimode optical fiber 140 at the point x, i.e., for light transmitted into fiber mode "j" and then, received from fiber mode "i". Such a response function does not always determine the single-direction, transfer matrix H of the multimode optical fiber 140, because roundtrip propagation may introduce, e.g., phase ambiguities in the relationship between single-direction and roundtrip transfer matrices.

Steps 510-520 of method 500 implement a recursive algorithm, using which the fiber transfer matrix H is estimated from the response matrices $A_q$ of step 508, e.g., in a manner that removes phase ambiguities. The algorithm is based on an approximation according to which, for any spatially resolved pair of coordinates $(x_q, x_{q+1})$, i.e., which are locations of the left and right ends of a corresponding segment of the optical fiber 140 whose length is $|x_q - x_{q+1}|$, is assumed to be sufficiently small. In particular, differences between the phase changes of the different fiber modes in each successive pair of such segments, e.g., the segment with coordinates $(x_q, x_{q+1})$ and the segment with coordinates $(x_{q+1}, x_{q+2})$, are, e.g., smaller than $\pi$. That is, each fiber segment for a successive pair of coordinates, in the set $\{x_1, \ldots, x_Q\}$, is short enough to not cause phase ambiguities in determinations of the elements of the single-direction transfer matrices therefrom. A person of ordinary skill in the art will understand that the validity of the algorithm can be enforced, inter alia, by: (i) properly designing DBR reflectors 210 or 310; (ii) employing photodetectors 156 having a relatively large bandwidth; and (iii) acquiring sufficiently large sets $S_{ij}$ at step 410 of method 400 using a relatively fast ADC 160.

Step 510 serves to initiate the above-mentioned recursive algorithm by setting the index q to a suitable initial value, e.g., q=0.

Step 512 serves to verify that the index (q+1) is within the valid range, which is defined as $1 \leq q \leq Q$. If the index (q+1) is within the valid range, then the processing of method 500 is directed to step 514. Otherwise, the processing of method 500 is directed to step 520.

At step 514, the matrices $P_L$ and $P_R$ are computed, e.g., in DSP 170, as follows.

If q=0, then $P_L = P_R = I_N$, where $I_N$ is the N×N identity matrix.

If q=1, then $P_L = H_1^T$ and $P_R = H_1$.

If q>1, then the matrices $P_L$ and $P_R$ are computed in accordance with Eqs. (6) and (7):

$$P_L = \prod_{k=1}^{q} H_k^T \qquad (6)$$

-continued $$P_R = \prod_{k=q}^{1} H_k \quad (7)$$

where the matrix $H_k$ is the transfer matrix of the k-th successive fiber segment; and the superscript T denotes the transposed matrix.

At step 516, the matrix $H_{q+1}$ is computed by numerically and iteratively solving Eq. (8):

$$P_L \times H_{q+1}^T \times H_{q+1} \times P_R = A_{q+1} \quad (8)$$

At step 518, the index q is incremented by one. The processing of method 500 is then directed back to step 512.

At step 520, the estimate of the transfer matrix H is computed using Eq. (9):

$$H = \prod_{k=Q}^{1} H_k \quad (9)$$

The computed transfer matrix H is then saved in memory 180 for future use, and the processing of method 500 is terminated.

Method 500 may include performing one or more iterations of at least some steps or sequences of steps shown in FIG. 5 to ensure that the final single-direction transfer matrix H has been properly computed, i.e., to remove the risk of any phase ambiguities. For example, as described, method 500 involves initially selecting a set of Q successive points $\{x_1, x_2, \ldots, x_Q\}$, i.e., $x_1 < x_2 < \ldots < x_Q$ along the multimode optical fiber 140, at which corresponding values of the matrix $A_{ij}(x_q)$ are used to subsequently iteratively, multiplicatively determine the value of H. After determining H, method 500 may be repeating some of the steps for a new larger set of 2Q successive points $\{x_1, x_2, \ldots, x_{2Q}\}$ along the fiber, wherein the distance between the successive ones of the points is smaller than the distance between the successive ones of the original Q points, e.g., successive separations may be ½ of the original ones in the new set of 2Q points. If the new set of 2Q successive points along the multimode optical fiber 140 leads to a determination of the single-direction transfer matrix H with elements having about the same values, i.e., below threshold differences in amplitudes and phases of the re-determined matrix elements, method 500 is terminated. Otherwise, method 500 may be repeated by again doubling the total number of points along the optical fiber 140, which are used for values of the matrix $A_{ij}(x_q)$ and for the iterative and multiplicative determination of the single-direction transfer H as explained in reference to equations (6)-(9), i.e., for yet shorter segments of the multimode optical fiber 140.

According to an example embodiment disclosed above, e.g., in the summary section and/or in reference to any one or any combination of some or all of FIGS. 1-5, provided is an apparatus comprising: a tunable laser (e.g., 104, FIG. 1) configured to generate probe light and controllable to sweep a wavelength of said probe light; a first configurable optical filter (e.g., 132, FIG. 1) to transmit a received part of said probe light primarily to a selectable spatial propagation mode of the multimode optical fiber at a first end thereof; a second configurable optical filter (e.g., 136, FIG. 1) to receive light from the first end of the multimode optical fiber in response to reflection therein and to transmit a portion of said received light, said portion being primarily received from a chosen spatial propagation mode of said multimode optical fiber at the first end; an optical interferometer (e.g., 120, FIG. 1) connected to mix other part of the probe light with the light transmitted by the second configurable optical filter to generate an optical interference signal; and a digital signal processor (e.g., 170, FIG. 1) configured to determine a single-direction transfer matrix of said multimode optical fiber from measurements of said optical interference signal.

In some embodiments of the above apparatus, the apparatus further comprises the multimode optical fiber (e.g., 140, FIGS. 1-3), the multimode optical fiber having reflectors distributed along at least a portion thereof (e.g., 210, FIG. 2; 310, FIG. 3).

In some embodiments of any of the above apparatus, the multimode optical fiber has a grating (e.g., 210, FIG. 2) distributed over at least half of the length of the multimode optical fiber.

In some embodiments of any of the above apparatus, the multimode optical fiber has spatially separated gratings (e.g., 310, FIG. 3) distributed over at least half of the length of the multimode optical fiber.

In some embodiments of any of the above apparatus, the apparatus further comprises an optical endoscope and an apparatus for forming images with light received from the optical endoscope, the optical endoscope including the multimode optical fiber.

In some embodiments of any of the above apparatus, the apparatus is capable of performing optical coherence tomography imaging with light received from the multimode optical fiber.

In some embodiments of any of the above apparatus, the apparatus further comprises an electronic controller (e.g., 190, FIG. 1) capable of causing the first and second configurable optical filters to change at least one of the selectable spatial propagation mode and the chosen spatial propagation mode.

In some embodiments of any of the above apparatus, the apparatus is configured to measure said optical interference signal in a manner that is sensitive to polarization state of the light of the chosen spatial propagation mode.

In some embodiments of any of the above apparatus, the digital signal processor is configured to estimate the single-direction transfer matrix of the multimode optical fiber using estimates of transfer matrices of different segments of the multimode optical fiber.

In some embodiments of any of the above apparatus, the digital signal processor is further configured to estimate roundtrip transfer matrices for the different segments of the multimode optical fiber, each of the roundtrip transfer matrices being a transfer matrix for light reflected at a corresponding end region of a respective fiber segment.

In some embodiments of any of the above apparatus, the apparatus further comprises a mode-selective multiplexer (e.g., 132, FIG. 1) that includes the first configurable optical filter.

In some embodiments of any of the above apparatus, the apparatus further comprises a mode-selective demultiplexer (e.g., 136, FIG. 1) that includes the second configurable optical filter.

According to another example embodiment disclosed above, e.g., in the summary section and/or in reference to any one or any combination of some or all of FIGS. 1-5, provided is an apparatus comprising: an optical frequency-domain reflectometer having a tunable light source (e.g., 104, FIG. 1), an optical interferometer (e.g., 120, FIG. 1), and an optical receiver (e.g., 150, FIG. 1), the optical interferometer including a multimode optical fiber (e.g., 140, FIGS. 1-3) having reflectors (e.g., 210, FIG. 2; 310, FIG. 3) distributed there along, the optical interferometer being configured to generate output light (e.g., 128, FIG. 1) in response to receiving probe light from the tunable light source, the apparatus being able to selectively form the output light to primarily correspond to light transmitted to a selected spatial propagation mode at an end of the multimode optical fiber and light outputted at the end of the multimode optical fiber from a chosen spatial propagation mode of the multimode optical fiber; and a digital signal processor (e.g., 170, FIG. 1) configured to estimate a single-direction fiber transfer matrix (e.g., H, at 520, FIG. 5) in response to measurements of the output light performed by the optical receiver.

In some embodiments of the above apparatus, the digital signal processor is configured to estimate the single-direction fiber transfer matrix using estimates of transfer matrices of segments of the multimode optical fiber of different lengths.

In some embodiments of any of the above apparatus, the digital signal processor is configured to determine roundtrip optical transfer matrices of segments of said multimode optical fiber of different lengths, wherein the roundtrip optical transfer matrix of each one of the segments is a transfer matrix for light reflected back near a distal end of the segment.

In some embodiments of any of the above apparatus, the reflectors include a plurality of spatially separated Bragg gratings (e.g., $310_k$, FIG. 3), the Bragg gratings being distributed over at least half of the length of the multimode optical fiber.

In some embodiments of any of the above apparatus, the reflectors include a Bragg grating (e.g., 210, FIG. 2) extending along at least half of the length of the multimode optical fiber.

In some embodiments of any of the above apparatus, the apparatus further comprises an optical endoscope including the multimode optical fiber; and wherein the apparatus is capable of producing optical images with light received from the multimode optical fiber.

In some embodiments of any of the above apparatus, the apparatus is configured to perform optical coherence tomography imaging with light received via the multimode optical fiber.

According to yet another example embodiment disclosed above, e.g., in the summary section and/or in reference to any one or any combination of some or all of FIGS. 1-5, provided is an apparatus comprising: a tunable laser (e.g., 104, FIG. 1) configured to generate probe light whose wavelength is swept from a first wavelength to a second wavelength (e.g., $\lambda_1$ and $\lambda_2$ respectively, Eq. (4)); an interferometer (e.g., 120, FIG. 1) connected to receive the probe light from the tunable laser and apply output light to an optical receiver (e.g., 150, FIG. 1), the output light being generated using optical interference between respective portions of the probe light after said respective portions pass through a reference arm (e.g., $124_1$, FIG. 1) and a measurement arm (e.g., $124_2$, FIG. 1) of the interferometer, respectively; and a multimode optical fiber (e.g., 140, FIGS. 1-3) having distributed reflectors (e.g., 210, FIG. 2; 310, FIG. 3) therein, a proximal end of the multimode optical fiber being connected to the measurement arm; wherein the interferometer comprises: a first configurable mode-selective filter (e.g., 132, FIG. 1) connected to select a guided mode of the multimode optical fiber into which the measurement arm couples the probe light through the proximal end; and a second configurable mode-selective filter (e.g., 136, FIG. 1) connected to select a guided mode of the multimode optical fiber for generating the output light by filtering a portion of the probe light reflected by the distributed reflectors and received by the measurement arm through the proximal end.

In some embodiments of the above apparatus, the apparatus further comprises an electronic controller (e.g., 190, FIG. 1) connected to cause the first and second configurable mode-selective filters to change at least one of the selected guided modes.

In some embodiments of any of the above apparatus, the optical receiver is polarization-sensitive.

In some embodiments of any of the above apparatus, the reference arm includes a polarization controller (e.g., 125, FIG. 1).

In some embodiments of any of the above apparatus, the distributed reflectors include a plurality of distinct distributed Bragg gratings (e.g., $310_k$, FIG. 3).

In some embodiments of any of the above apparatus, the apparatus further comprises a digital signal processor configured to estimate a fiber transfer matrix (e.g., H, at 520, FIG. 5) in response to measurements of the output light performed by the optical receiver.

In some embodiments of any of the above apparatus, the digital signal processor is configured to estimate the fiber transfer matrix using estimates of segment transfer matrices (e.g., $H_k$, Eqs. (6)-(9); computed at 516, FIG. 5) corresponding to individual segments of the multimode optical fiber located between different ones of the distributed reflectors.

In some embodiments of any of the above apparatus, the apparatus further comprises a mode-selective multiplexer (e.g., 132, FIG. 1) that includes the first configurable mode-selective filter.

In some embodiments of any of the above apparatus, the apparatus further comprises a mode-selective demultiplexer (e.g., 136, FIG. 1) that includes the second configurable mode-selective filter.

According to yet another example embodiment disclosed above, e.g., in the summary section and/or in reference to any one or any combination of some or all of FIGS. 1-5, provided is an apparatus comprising: an optical frequency-domain reflectometer having a tunable light source (e.g., 104, FIG. 1), an interferometer (e.g., 120, FIG. 1), and an optical receiver (e.g., 150, FIG. 1), the interferometer including a multimode optical fiber (e.g., 140, FIGS. 1-3) having distributed reflectors (e.g., 210, FIG. 2; 310, FIG. 3) therein, the interferometer being configured to generate output light (e.g., 128, FIG. 1) in response to probe light received from the tunable light source, the output light being sensitive to guided modes of the multimode optical fiber controllably selected in the interferometer; and a digital signal processor (e.g., 170, FIG. 1) configured to estimate a fiber transfer matrix (e.g., H, at 520, FIG. 5) in response to measurements of the output light performed by the optical receiver.

In some embodiments of the above apparatus, the digital signal processor is configured to estimate the fiber transfer matrix using estimates of segment transfer matrices (e.g., $H_k$, Eqs. (6)-(9); computed at 516, FIG. 5) corresponding to individual segments of the multimode optical fiber located between different ones of the distributed reflectors.

In some embodiments of any of the above apparatus, the distributed reflectors include a plurality of distinct distributed Bragg gratings (e.g., $310_k$, FIG. 3).

While this disclosure includes references to illustrative embodiments, this specification is not intended to be construed in a limiting sense. Various modifications of the described embodiments, as well as other embodiments within the scope of the disclosure, which are apparent to persons skilled in the art to which the disclosure pertains are deemed to lie within the principle and scope of the disclosure, e.g., as expressed in the following claims.

Some embodiments can be embodied in the form of methods and apparatuses for practicing those methods. Some embodiments can also be embodied in the form of program code recorded in tangible media, such as magnetic recording media, optical recording media, solid state memory, floppy diskettes, CD-ROMs, hard drives, or any other non-transitory machine-readable storage medium, wherein, when the program code is loaded into and executed by a machine, such as a computer, the machine becomes an apparatus for practicing the patented invention(s). Some embodiments can also be embodied in the form of program code, for example, stored in a non-transitory machine-readable storage medium including being loaded into and/or executed by a machine, wherein, when the program code is loaded into and executed by a machine, such as a computer or a processor, the machine becomes an apparatus for practicing the patented invention(s). When implemented on a general-purpose processor, the program code segments combine with the processor to provide a unique device that operates analogously to specific logic circuits.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain the nature of this disclosure may be made by those skilled in the art without departing from the scope of the disclosure, e.g., as expressed in the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the disclosure. The appearances of the phrase "in one embodiment" in various places in the specification are not necessarily all referring to the same embodiment, nor are separate or alternative embodiments necessarily mutually exclusive of other embodiments. The same applies to the term "implementation."

Unless otherwise specified herein, the use of the ordinal adjectives "first," "second," "third," etc., to refer to an object of a plurality of like objects merely indicates that different instances of such like objects are being referred to, and is not intended to imply that the like objects so referred-to have to be in a corresponding order or sequence, either temporally, spatially, in ranking, or in any other manner.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements. The same type of distinction applies to the use of terms "attached" and "directly attached," as applied to a description of a physical structure. For example, a relatively thin layer of adhesive or other suitable binder can be used to implement such "direct attachment" of the two corresponding components in such physical structure.

The described embodiments are to be considered in all respects as only illustrative and not restrictive. In particular, the scope of the disclosure is indicated by the appended claims rather than by the description and figures herein. All changes that come within the meaning and range of equivalency of the claims are to be embraced within their scope.

A person of ordinary skill in the art would readily recognize that steps of various above-described methods can be performed by programmed computers. Herein, some embodiments are intended to cover program storage devices, e.g., digital data storage media, which are machine or computer readable and encode machine-executable or computer-executable programs of instructions where said instructions perform some or all of the steps of methods described herein. The program storage devices may be, e.g., digital memories, magnetic storage media such as a magnetic disks or tapes, hard drives, or optically readable digital data storage media. The embodiments are also intended to cover computers programmed to perform said steps of methods described herein.

The description and drawings merely illustrate the principles of the disclosure. It will thus be appreciated that those of ordinary skill in the art will be able to devise various arrangements that, although not explicitly described or shown herein, embody the principles of the disclosure and are included within its spirit and scope. Furthermore, all examples recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions. Moreover, all statements herein reciting principles, aspects, and embodiments of the disclosure, as well as specific examples thereof, are intended to encompass equivalents thereof.

The functions of the various elements shown in the figures, including any functional blocks labeled as "processors" and/or "controllers," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

As used in this application, the term "circuitry" may refer to one or more or all of the following: (a) hardware-only circuit implementations (such as implementations in only analog and/or digital circuitry); (b) combinations of hardware circuits and software, such as (as applicable): (i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions); and (c) hardware circuit(s) and or processor(s), such as a microprocessor(s) or a portion of a microprocessor(s), that requires software (e.g., firmware) for operation, but the software may not be present when it is not needed for operation." This definition of circuitry applies to all uses of this term in this application, including in any claims. As a further example, as used in this application, the term circuitry also covers an implementation of merely a hardware circuit or processor (or multiple processors) or portion of a hardware circuit or processor and its (or their) accompanying software and/or firmware. The term circuitry also covers, for example and if applicable to the particular claim element, a baseband integrated circuit or processor integrated circuit for a mobile device or a similar integrated circuit in server, a cellular network device, or other computing or network device.

It should be appreciated by those of ordinary skill in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

As used herein and in the claims, the term "provide" with respect to a system, device, or component encompasses designing or fabricating the system, device, or component; causing the system, device, or component to be designed or fabricated; and/or obtaining the system, device, or component by purchase, lease, rental, or other contractual arrangement.

What is claimed is:

1. An apparatus comprising:
   a tunable laser configured to generate probe light and controllable to sweep a wavelength of said probe light;
   a first spatial mode-selective optical filter to transmit a received part of said probe light primarily to a selectable spatial propagation mode of a multimode optical fiber at a first end thereof;
   a second spatial mode-selective optical filter to receive light from the first end of the multimode optical fiber in response to reflection therein and to transmit a portion of said received light, said portion being primarily received from a chosen spatial propagation mode of said multimode optical fiber at the first end;
   an optical interferometer connected to mix other part of the probe light with the light transmitted by the second spatial mode-selective optical filter to generate an optical interference signal; and
   a digital signal processor connected to receive measurements of said optical interference signal and configured to determine a single-direction transfer matrix of the multimode optical fiber from said measurements.

2. The apparatus of claim 1, further comprising the multimode optical fiber, the multimode optical fiber having reflectors distributed along at least a portion thereof.

3. The apparatus of claim 2, wherein the multimode optical fiber has a grating distributed over at least half of the length of the multimode optical fiber.

4. The apparatus of claim 2, wherein the multimode optical fiber has spatially separated gratings distributed over at least half of the length of the multimode optical fiber.

5. The apparatus of claim 2, further comprising an optical endoscope and an apparatus for forming images with light received from the optical endoscope, the optical endoscope including the multimode optical fiber.

6. The apparatus of claim 2, wherein the apparatus is capable of performing optical coherence tomography imaging with light received from the multimode optical fiber.

7. The apparatus of claim 1, further comprising an electronic controller capable of causing the first and second spatial mode-selective optical filters to change at least one of the selectable spatial propagation mode and the chosen spatial propagation mode.

8. The apparatus of claim 1, wherein the apparatus is configured to measure said optical interference signal in a manner that is sensitive to polarization state of the light of the chosen spatial propagation mode.

9. The apparatus of claim 8, wherein the digital signal processor is configured to estimate the single-direction transfer matrix of the multimode optical fiber using estimates of transfer matrices of different segments of the multimode optical fiber.

10. The apparatus of claim 9, wherein the digital signal processor is further configured to estimate roundtrip transfer matrices for the different segments of the multimode optical fiber, each of the roundtrip transfer matrices being a transfer matrix for light reflected at a corresponding end region of a respective fiber segment.

11. The apparatus of claim 1, further comprising a mode-selective multiplexer that includes the first spatial mode-selective optical filter.

12. The apparatus of claim 11, further comprising a mode-selective demultiplexer that includes the second spatial mode-selective optical filter.

13. The apparatus of claim 1, further comprising a mode-selective demultiplexer that includes the second spatial mode-selective optical filter.

* * * * *